United States Patent [19]
Kolesar et al.

[11] Patent Number: 6,013,442
[45] Date of Patent: Jan. 11, 2000

[54] DIRECT QUANTITATION OF LOW COPY NUMBER RNA

[76] Inventors: Jill M. Kolesar, 8074 Burr Oak Trail, Cross Plains, Wis. 53528; Peter G. Allen, 2525 University Avenue, Apt. F., Madison, Wis. 53705

[21] Appl. No.: 08/906,443

[22] Filed: Aug. 5, 1997

[51] Int. Cl.[7] .............................. C12Q 1/68; C12P 19/34
[52] U.S. Cl. ................................................ 435/6; 435/91.2
[58] Field of Search ........................... 435/5, 6; 536/22.1, 536/23.1

[56] References Cited

FOREIGN PATENT DOCUMENTS

| | | |
|---|---|---|
| 0 382 433 A2 | 2/1990 | European Pat. Off. . |
| 0 714 986 A1 | 5/1996 | European Pat. Off. . |
| WO 93/13223 | 8/1993 | WIPO . |

OTHER PUBLICATIONS

Database WPI, Section Ch, Week 9131, Derwent Publications Ltd., London, GB; Class B04, AN 91–227685, XP002084014 & JP 03 147797 A (Shimadzu Corp), Jun. 24, 1991, see abstract.

Fang C., et al., "Sequence–Dependent Separation of DNA Fragments by Capillary Electrophoresis in the Presence of SYBR® Green I", BioTechniques, vol. 23, Jul. 1997, pp. 58, 60.

Kolesar J.M., et al., "Direct quantification of HIV–1 RNA by capillary eletrophoresis with laser–induced fluorescence", Journal of Chromatography B, vol. 697, Sep. 12, 1997, pp. 189–194.

Coste et al., Comparative Evaluation of Three Assays for the Quantitation of Human Immunodeficiency Virus Type 1RNA in Plasman, J. Med. Virol. 50:234–302 (1996).

Schuurman et al., Multicenter Comparison of Three Commercial Methods for Quantification of Human Immunodeficiency Virus Type 1 RNA in Plasma, J. Clin. Microbiol. 34(12): 3016–22 (1996).

Mellors et al., Quantitation of HIV–1 RNA in Plasma Predicts Outcome after Seroconversions Ann. Intern. Med. 122:573–79 (1995).

Bianchi et al., Capillary Electrophoresis: Detection of Hybridization Between Synthetic Oligonucleotides and HIV–1 Gernomic DNA Amplified by Polymerase–Chain Reaction, J. Virol. Meth. 47:321–29 (1994).

Todd et al., Quantification of Human Immunodeficiency Virus Plasma RNA By Branched DNA and Reverse Transcription Coupled Polymerase Chain Reaction Assay methods; A Critical Evaluation of Accuracy and Reproducibility; Serodiagn. Immunother. Infect. Disease 6(4):233–39 (1994).

Fernandez–Arcas et al., Direct Quantification of HIV–1 RNA in Human Plasma by Free Solution Capillary Electrophoresis, J. Acq. Imm. Defic. Syn. Human Retrovir. 12:107–11 (1996).

Schwartz and Ulfelder, Capillary Electrophoresis with Laser–Induced Fluorescence Detection of PCR Fragments Using Thiazole Orange, Anal. Chem. 64:1737–40 (1992).

*Primary Examiner*—Eggerton A. Campbell
*Attorney, Agent, or Firm*—Michael Best & Friedrich LLP; Teresa J. Welch

[57] ABSTRACT

A direct quantitation of RNA contained in a sample is obtained by capillary electrophoresis of the RNA hybridized to a DNA probe of complementary sequence stabilized by the combination of a fluorophore terminally conjugated to the DNA probe and a dye intercalating the RNA-DNA hybrid so formed. The RNA is quantified by measuring the total fluorescence emitted by the electrophoresed hybrid upon excitation by a laser generated light beam.

7 Claims, 7 Drawing Sheets

DIRECT QUANTITATION OF LOW COPY NUMBER RNA

FIELD OF THE INVENTION

This invention relates to the field of direct nucleic acid detection, particularly RNA in low copy number, without a requirement for amplification of either the number of RNA molecules, or by amplification of a detection signal. The method further utilizes capillary electrophoresis to detect a target RNA-DNA probe hybrid band. The invention also combines laser-induced fluorescence and capillary electrophoresis.

BACKGROUND OF THE INVENTION

The quantitation of RNA, particularly RNA derived from infectious agents or from cellular sources, is important in the diagnosis and monitoring of disease states caused by such agents. For example, the viral load detected in serum correlates to high concentrations of virus in the lymph nodes and has predictive value in assessing progression of AIDS to advanced stages, as reported in Ho, et al., *Nature*, 373: 123 (1995) and Mellors, et al., *Ann. Intern. Med.*, 122: 573 (1996). Viral titers in serum are also correlated with disease progression for other viruses such as HCV, nonA nonB hepatitis other than HCV, and atypical lentiviruses.

There are several fundamental problems in RNA quantitation in low copy number. If there are too few molecules to detect by conventional means, amplification of the target sequence to increase its numbers by several logs is necessary. However, the coefficients of variability (CV) may often exceed 20 percent or more, so that the result obtained is unreliable, and does not correlate with the stage of disease. The coefficient of variability (CV) is defined as the standard deviation of the values obtained divided by the mean. Increased signal from a small number of target molecules is another approach, but the final result depends upon a large number of reactions which must occur in correct sequence. Again, there is a large CV because of reaction sequence errors giving a spectrum of values.

Alternatively, direct measurement of the low RNA copy number in the native sample, even where adequate detection sensitivities can be achieved, is thwarted by the inherent instability of RNA-DNA duplexes. Increasing the length of the hybridized target can increase both sensitivity and stability of the hybrid, but the additional nucleotide sequence combinations increase the chance of nonspecific hybridizing to fragments of host nucleic acids or partial hybridization to nonselected regions of the viral genome, thereby contributing to a falsely inflated positive value. Most of the improvements to date in low RNA copy number quantitation represent attempts to better control the multiple molecular events involved in signal or nucleic acid amplification strategies.

The three main amplification systems currently available include branched chain signal amplification (bDNA), reverse transcriptase polymerase chain reaction (RT-PCR), and nucleic acid sequence based amplification (NASBA). The strategy of the first two, bDNA and RT-PCR, involves using a first reaction step that converts the system from an RNA target to a DNA target.

In bDNA an initial probe hybridizing with a complementary probe contains a plurality of noncomplementary sites capable of hybridizing to further DNA strands, which in turn may hybridize sites noncomplementary to the probe sequence, so that as repeated layers of hybridization occur, a branched DNA structure of extreme complexity is created. The last to be annealed strand in the branched structure carries a reporter. Thus the original RNA target molecule gives rise to an amplification of the signal generating capability of the system. A full explanation and description of the bDNA technique is set forth in Fultz, et al., "Quantitation of plasma HIV-I RNA using an ultra sensitive branched DNA (bDNA) assay", in *Program and Abstracts of the 2nd National Conference on Human Retroviruses* (1995), and product literature, L-6170 Rev. 5.0 for the Quantiplex™ HIV-RNA Assay (Chiron Corporation).

In RT-PCR a cDNA is generated from the RNA template, and then an ordinary PCR amplification ensues utilizing selected primers to define the left and right ends of the amplicon. Each successive round of synthesis and denaturation causes an exponential increase in the number of progeny strands generated in the system. After the amplification is complete, a probe having a complementary sequence to some portion of the amplicon and carrying a reporter can be used for detecting the amplified target. In both RT-PCR and bDNA, the original RNA target can theoretically be dispensed with, without impairing the sensitivity of the test, once the conversion to a DNA system has occurred. These methods effectively get around the inherent lability of the RNA target or its RNA-DNA duplex hybrid.

Similarly, both RT-PCR and bDNA share many of the same deficiencies. Both systems rely upon the integrity of a large number of successive hybridization events. If an early hybridization event fails, for any of a number of reasons such as structural (steric) hindrance, uncorrected mismatch, binding of a defective enzyme molecule, etc., the final number of copies, and therefore the intensity of the signal will be ablated. These random occurrences help to account for the great sensitivity of the assays coupled with a widely variable coefficient of variability. The commercial form of the test normalizes variability by co-amplification of an internal standard. To control for variability the internal standard must be amplified under identical conditions as the target yet be able to be differentiated from the target, an almost impossible task. Also, introducing an internal standard changes the PCR reaction kinetics itself. RT-PCR, while showing some efficacy, is in practice very labor intensive, and not practical under normal clinical laboratory conditions.

In NASBA, the lability of RNA is overcome by increasing copy number to a vast number. The technique involves creating a cDNA from the target RNA and then generating a large number of transcripts from bDNA template, which in turn can be converted to a cDNA, and so on. The number of transcripts produced is always much greater than the number converted to cDNA, so that a large excess of RNA occurs. The process is initiated upon annealing of two primers, one of which contains a phage promoter, which in the ensuing cDNA provides a point of initiation for transcription. Unlike PCR where the numbers of actual cycles of amplification are nominally controlled by the number of temperature cycles, there is much less control in NASBA. The technique suffers from a lack of uniformity as between different target sequences, and in the same target sequence from one run to another. The commercial form of the assay employs three internal calibrators, which are co-amplified with the target sequence. In any detection technique it is desirable for the analytical coefficient of variability (CV) to be less than 15 percent.

The three techniques were recently compared in a study by Coste, et al., *J. Med. Virol.*, 50: 293 (1996). bDNA was found to be most reproducible with CVs ranging from 6–35 percent. Better results were achieved at high copy number, 12.4% vs. 31% for low copy number. However, sensitivity was only 68 percent with a lower level of detection at 4000 HIV equivalents. NASBA was the least reliable test with CVs ranging from 13–62 percent, with CV averages of 20.7 percent for high copy number and 41.8 percent for low copy number. Sensitivity was 100 percent with a lower level of detection at 2600 HIV equivalents. Finally, RT-PCR has a sensitivity of 93 percent, but a mean CV of 43 percent.

While improvements in the foregoing techniques may result from optimization of the operating conditions of the assays, and from discovery of reagent combinations that minimize interferences with hybridizations, it is unlikely that variability will ever be reduced uniformly to coefficient values less than 15 percent. This is because priming errors and hybridization interferences cannot be entirely overcome, and misevents occurring early in the sequence of amplification steps have a geometric impact on the result. Thus the wide range of CV. If the level of sensitivity for direct detection of RNA could be increased by several orders of magnitude over standard UV detection methods, and the problem of RNA-DNA duplex instability be solved, direct detection would provide a viable alternative to current amplification-based methods without loss of reliability.

SUMMARY OF THE INVENTION

In the method of the present invention, two different dye molecules are utilized to produce a characteristic signal emission upon excitation with a laser beam. RNA is extracted from a cell-free biological specimen such as serum or from a cellular RNA source, hybridized to a fluorescent DNA probe (first dye molecule covalently attached to probe) of complementary sequence to form an RNA-DNA hybrid, applied as the hybrid RNA-DNA duplex to a capillary electrophoresis column, electrophoresing in a hybrid band in the presence of an intercalating dye (second dye in electrophoresis buffer), and quantitatively detecting the amount of RNA-DNA hybrid by measuring the total fluorescent intensity of light emitted from the hybrid band upon excitation by laser-induced fluorescence, and decay of the excited molecules to light of a longer wave length.

In capillary electrophoresis, the sample containing the RNA-DNA hybrid is loaded onto the gel column and an electric current is applied to the gel matrix. The dye which permeates the gel matrix, is capable of intercalating the hybrid, and binds to the interstices of the duplex, so that these intercalated molecules migrate with the hybrid band. The unbound dye molecules are not seen as background because its quantum yield varies in the presence of nucleic acid. The band is quantitated by directing a scanning laser-induction beam along the gel. The hybrids with pendant dye (both covalently attached and bound by electrostatic interaction), migrating as a band, absorb the light of excitation wavelength, and emit at a lower energy wavelength. Peak areas of light emission intensity are identified. The total fluorescence is the sum of the fluorescence values under the peak.

Applicants have discovered that the configuration of terminal labelling of the DNA probe with one dye type, and allowing intercalating of the duplex hybrid by a second dye type has the unexpected benefit of dramatically increasing the stability of the hybrid. Hence, the present invention provides a method for stabilizing during capillary electrophoresis nucleic acid hybrids consisting of an RNA strand and a fluorophore terminally labelled DNA strand of short length (15 to about 40 base pairs in length) which involves only electrophoresing the nucleic acid hybrid in the presence of an intercalating dye. Any dye, preferably which fluoresces at the same wavelength as the dye covalently attached to the DNA probe, capable of intercalating double stranded nucleic acids will be efficacious in increasing stability. The ability to stabilize short RNA-DNA duplexes means that an RNA target sequence can now readily be selected having less than 5 percent homology to any other portion of the target, and non-homology to host nucleic acids, as verified by a GenBank search or by comparison to other published sequence databases.

The present invention also provides a kit containing the key ingredients for carrying out a direct quantitative test for HIV-1 and other targets suspected of being present in a biological specimen utilizing capillary electrophoresis and laser-induced fluorescence. The kit contains a quantity of a DNA probe of 15 to 30 nucleotides labelled with a fluorophore at its 3',5' terminus, or at both termini, whose sequence is complementary to an RNA sequence having less than 5% homology to any other sequence of commensurate length contained within the target gene, or other host genome. The kit also provides a quantity of a fluorescent dye capable of intercalating an RNA-DNA hybrid molecule of 15–30 base pairs. The vessels containing the reagent probe and dye are made of materials to which the reagents do not adhere, such as surface-treated borosilicate glass, polypropylene and the like, and are shaped to accommodate an automatic pipetter tip.

The methods and reagents of the present invention fulfill the following advantages and objectives:

fast and highly reliable direct assay for quantitative determination of RNA a low coefficient of variability even at low copy number of RNA lower cost than amplification-based tests greater sensitivity than any other direct gene quantitation method.

BRIEF DESCRIPTION OF THE DRAWINGS

FIGS. 1A–1C are electropherograms of cellular RNA (1.856 µg/µL) obtained from *Spodoptera frugiperda* culture. FIG. 1A represents an injection at time 0. A second injection of same sample after 30 minutes at room temperature is shown in FIG. 1B. FIG. 1C shows a third injection of same sample after 60 minutes at room temperature.

FIGS. 3A–3C show an electropherogram analysis of hybridization products. RNA samples obtained from a HIV seropositive patient and a seronegative volunteer were hybridized with a HIV specific probe and analyzed as described in experimental. FIG. 3A represents a HIV RNA/Probe complex elutes at 12 min, indicating the presence of HIV RNA in the patient's serum. FIG. 3B represents a seronegative volunteer. FIG. 3C is a negative control containing all reaction components except RNA.

DETAILED DESCRIPTION OF THE PREFERRED EMBODIMENT

Figure 1A:
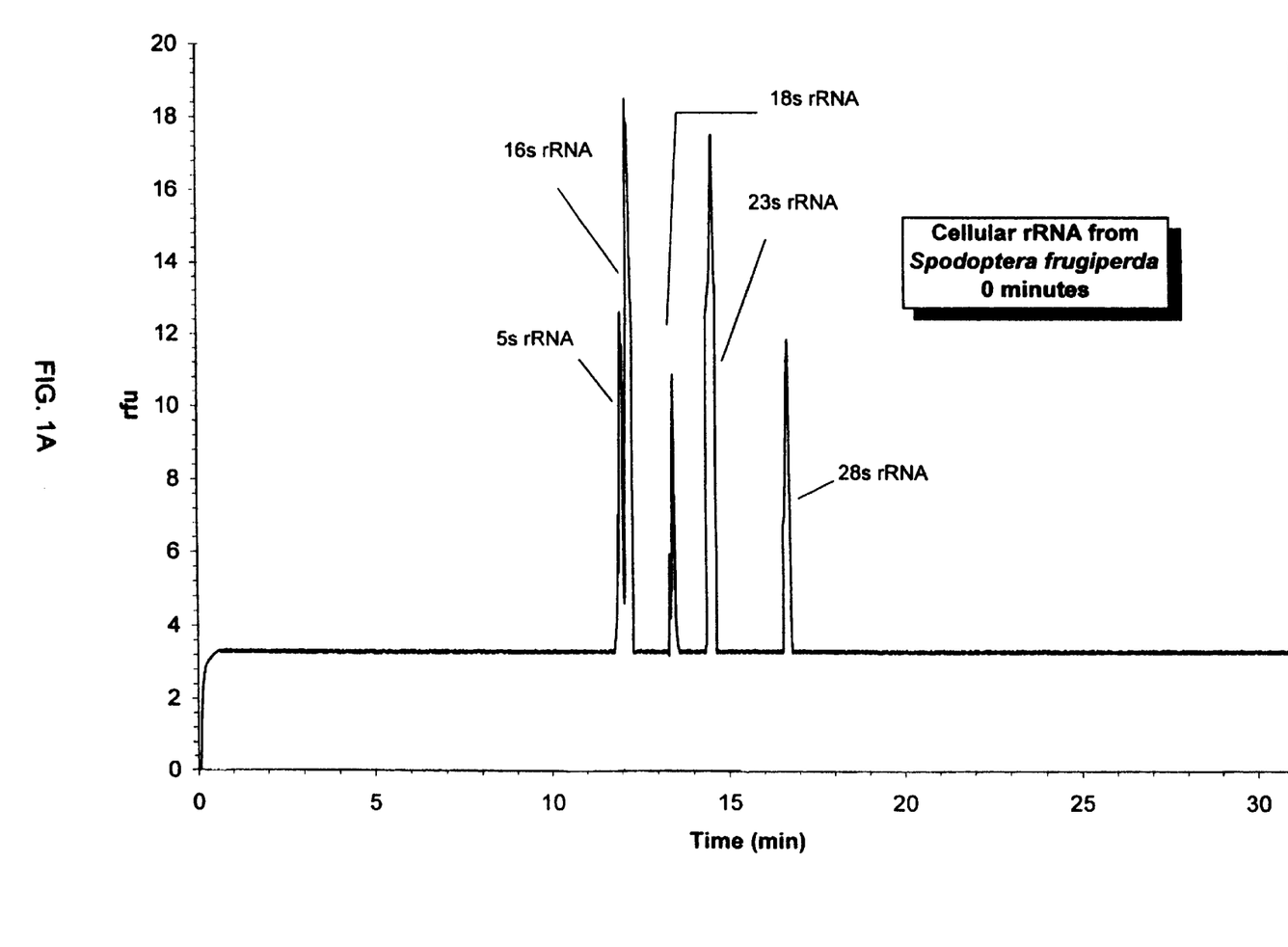
Figure 1B:
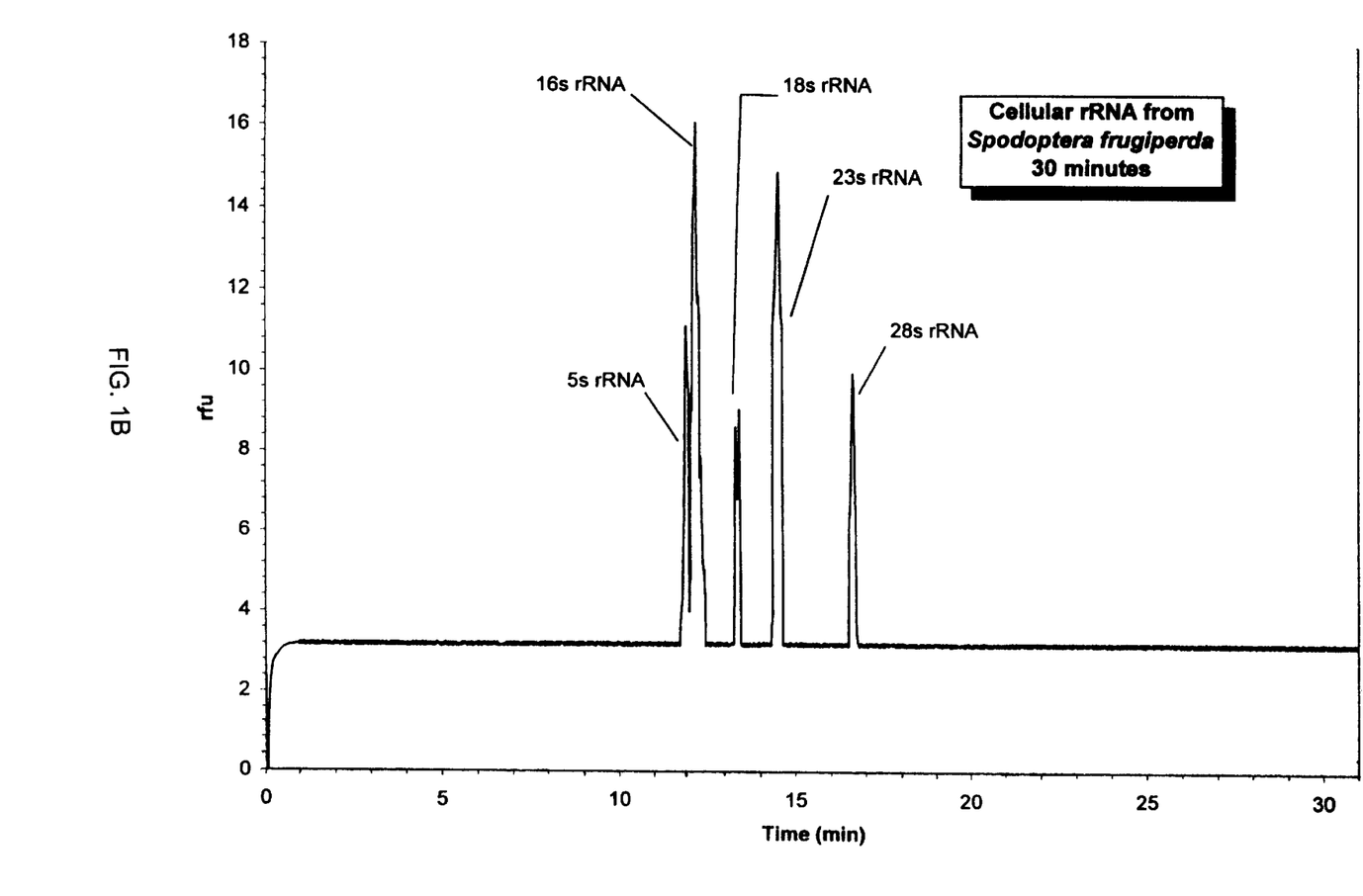
Figure 1C:
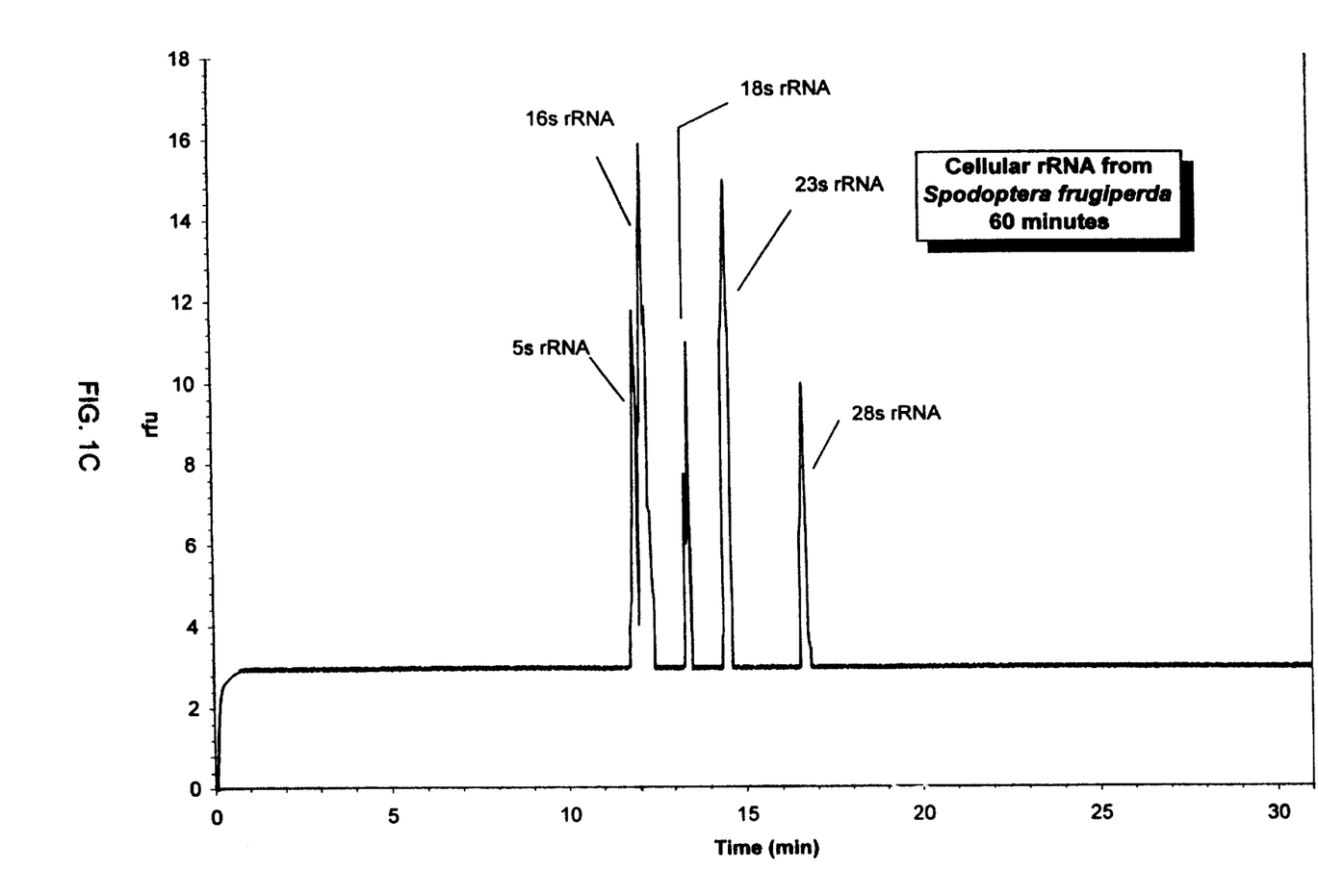
Figure 2:
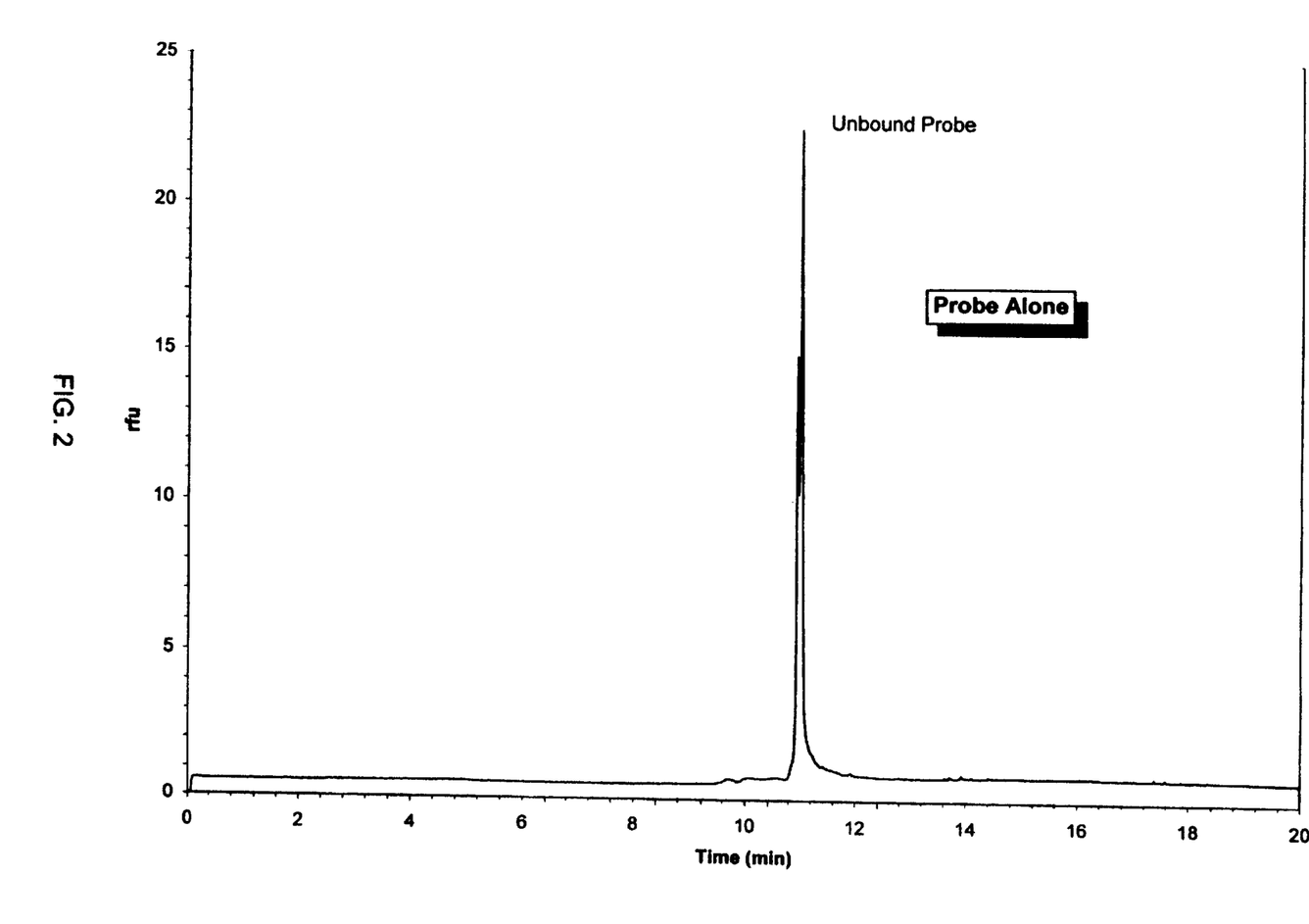
FIG. 2 is an electropherogram analysis of fluorescently labeled HIV specific probe alone diluted in DEPC treated water to a concentration of 72 fg/7.1 nL, which elutes at 11 min.
Figure 3A:
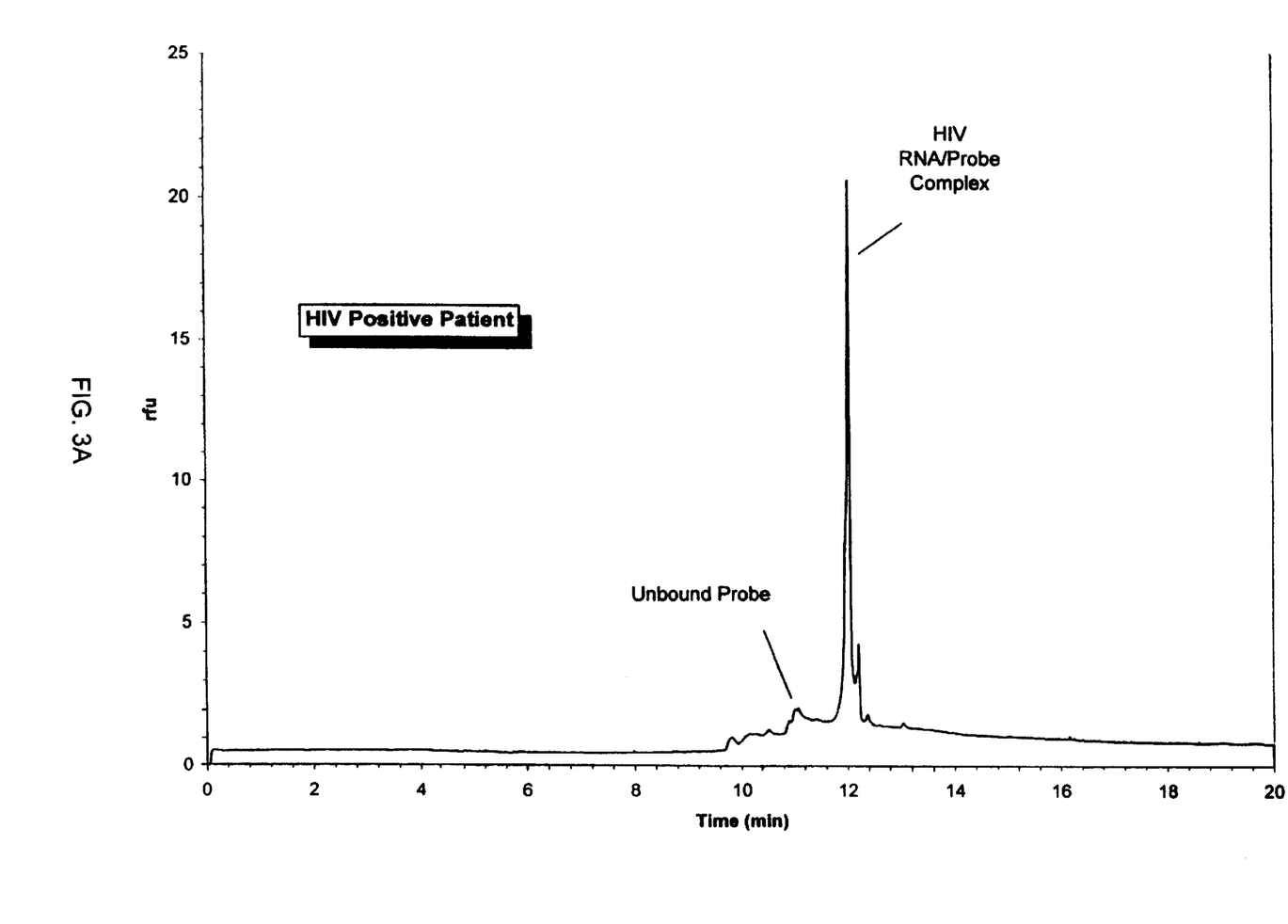
Figure 3B:
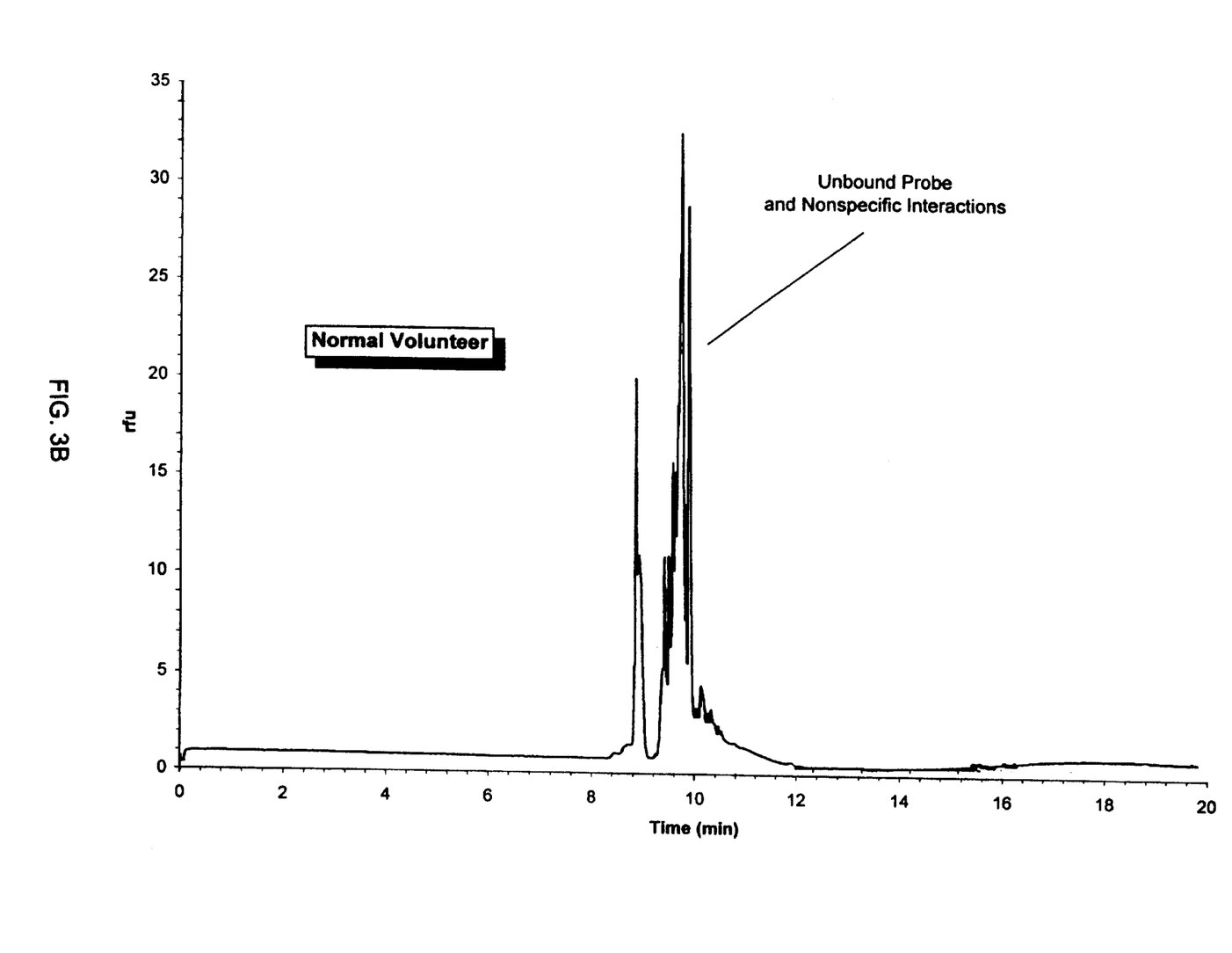
Figure 3C:
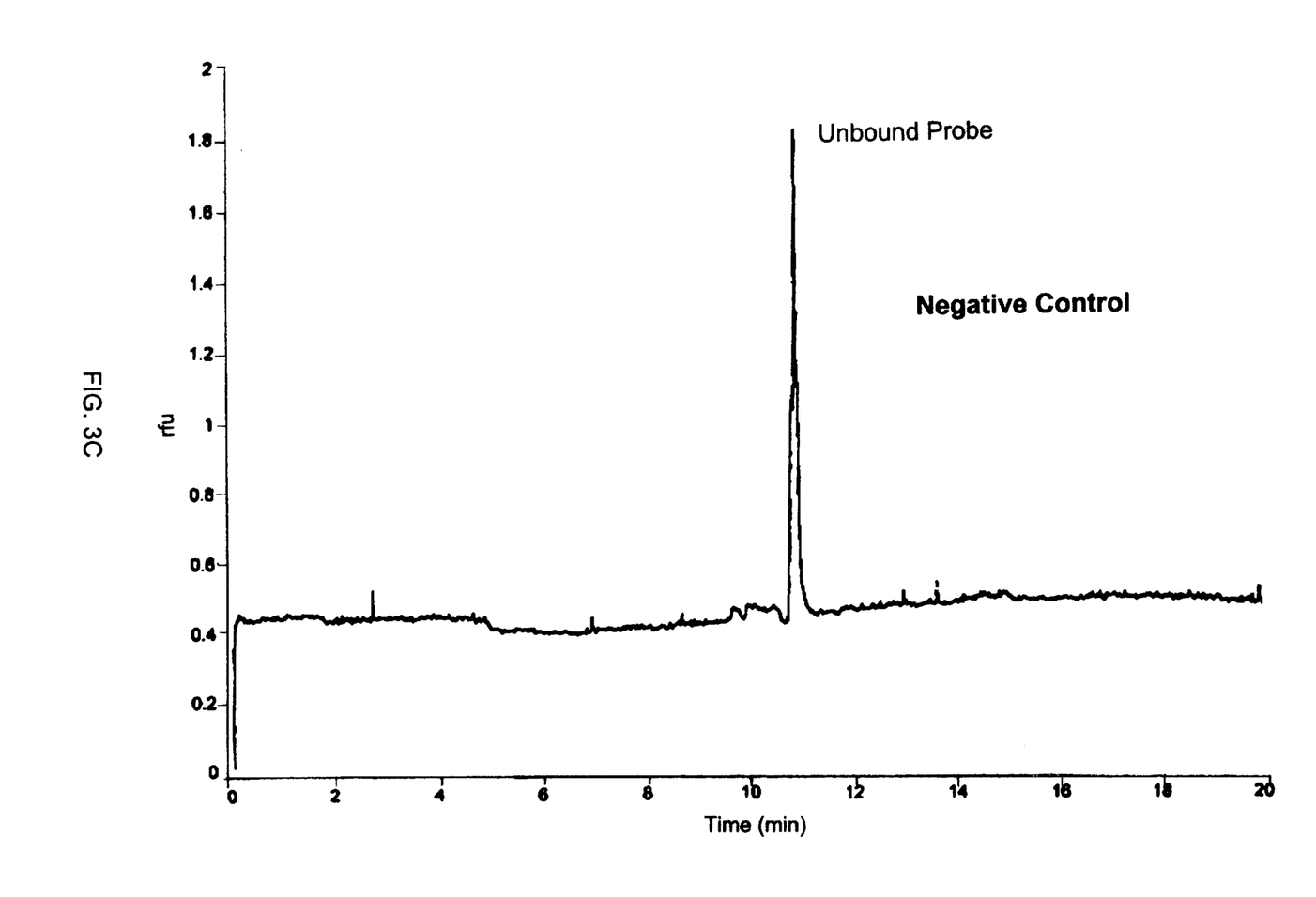

A basic problem in direct gene quantitation which Applicants have overcome is the extreme lability of target RNA-DNA duplexes under conditions of electrophoresis. Interestingly, the use of carrier RNA to stabilize the target RNA and the double stranded nucleic acid of the hybrid, is unavailing. Experiments utilizing carrier RNA, as set forth in Example 3, Table 4, show that there is no stabilization of the RNA-DNA hybrid having the sequence of Seq. I.D. No. 1 in the presence of carrier. Normally, carrier nucleic acid or protein, in the case of proteinaceous targets, function as a coprecipitant, or compete for a degradative enzyme, thereby protecting the target species through shear overwhelming numbers. Failure of carrier RNA to mitigate degradation of the hybrid is consistent with the conclusion that the RNA-DNA hybrid of short length is inherently unstable, and its lability is not due to a contaminating nuclease, or other process for which a carrier population can exert protection or rescue. Since the lability appears to be activated by the electric current, separation of tRNA from duplex may cause a loss of whatever protection might otherwise be afforded.

Isolating RNA from biological specimens may be carried out by any conventional method which takes precautions in minimizing RNA degradation. Accordingly, procedures involving heat or strong acid/base reagents are to be avoided. In preparing specimens from serum, blood is centrifuged to remove cells, and then extracted. There are several extraction kits commercially available for this purpose, as, for example, the Ultraspec II RNA isolation system from Biotex.

The probe sequence is selected for uniqueness within the genome of the organism to be detected and monitored, and which is unlikely to show any homology for the host genome. This is important because it is impossible to guarantee that all cells contained in the specimen will be removed by centrifugation. The degree of homology between the probe sequence and the remainder of the target genome should be as low as possible, but less than 5 percent. Thus, it is important to select a sequence long enough to confer selectivity and short enough to avoid partial homologies with non-target RNAs.

The DNA probe will have a nucleotide sequence of about 15 to 50 bases, preferably between 20 and 30 bases. In the case of HIV-1, a unique, genetically stable 26 base sequence from the pol gene was selected, having the sequence 5'-ACAGTATTAGAAGAYATGRRTTTGCC-3' (Seq. I.D. No. 1) (in which Y=A or C; and R=A or G). This sequence is identified in GenBank as entry U62632. A probe terminally labelled with a fluorophore at the 5' end and having the sequence given above which is complementary to the HIV-1 sense strand was prepared synthetically utilizing 5'-fluorescein phosphoramidite. Another sequence of interest in HIV quantitation is:

5'-GGCAAARRCATYTCTTCTAATACTGT-3' (Seq. I.D. No. 2).

Also, the following sequences are useful in the present invention for quantitation of Quinone Acceptor Oxidoreductase and Human Topoisomerase I, respectively.

NAD(P)H:
5'-TCGGACCTCTATGCCATGAACT-3' Seq. I.D. No. 3
5'-AGTTCATGGCATAGAGGTCCGA-3' Seq. I.D. No. 4
5'-AGGCTGGTTTGAGCGAGTGTTC-3' Seq. I.D. No. 5
5'-GAACACTCGCTCAAACCAGCCT-3' Seq. I.D. No. 6
5'-CAGCAGACGCCCGAATTCAAAT-3' Seq. I.D. No. 7
5'-ATTTGAATTCGGGCGTCTGCTG-3' Seq. I.D. No. 8
Human Topoisomerase I:
5'-AGAGACCTCGAGATGAGGATGA-3' Seq. I.D. No. 9
5'-TCATCCTCATCTCGAGGTCTCT-3' Seq. I.D. No. 10
5'-TCTCGTATTTCTGCCAGTCCTT-3' Seq. I.D. No. 11
5'-AAGGACTGGCAGAAATACGAGA-3' Seq. I.D. No. 12

Applicants sought to utilize an intercalating fluorescent dye to visualize a band of probed RNA migrating on an electrophoresis column. It was found, however, that for short (15–30) base pairs neither a fluorescein labelled DNA probed RNA duplex without intercalating dye, or a non-terminally labeled DNA probed RNA duplex in the presence of an intercalating dye alone was stable during electrophoresis. However, the combination of a terminally fluorophore labeled DNA probe and the presence of an intercalating fluorescent dye produced remarkable stability of the duplex, for reasons not yet understood.

The preferred terminal fluorophore is fluorescein, although others such as rhodamine, or the BODIPY series (Molecular Probes, Inc.) may be utilized also. The preferred intercalating dye is thiazole orange, although other dyes such as YOYO (also available from Molecular Probes, Inc., and whose structure is given at p.155 of its 1996 Catalogue for Product No. Y-3601) may be used. When using a laser-induced detection system, it is preferable from a sensitivity standpoint, to use terminating and intercalating dye pairs which emit light at the same wavelength, thereby boosting the signal additively, see Table 3. Fluorescein and thiazole orange absorb at 488 nm and emit at 520 nm. For probe manufacture, fluorescein is ideal because of its ease of use, well known coupling chemistries, and its low cost. Thiazole orange is more expensive, but in the capillary mode of electrophoresis, the small volumes reduce usage. In an alternate embodiment of the present method, the intercalating dye may be taken up by the DNA-RNA hybrid prior to loading on the gel.

Utilizing the combined dyes prevents degradation of the RNA-DNA hybrid, and also increases sensitivity to levels comparable to other methods. The most sensitive assay system will be the best system for monitoring HIV, and with a lower detection limit of 50 $\mu$g this system is more sensitive than other available methods. The lower limit of the linear range is 11 picograms to 72 femtograms, which provides a lower detection limit of 7200 HIV equivalents per ml compared to 10,000 equivalents for bDNA. The greater sensitivity of RT-PCR (350 equivalents/ml) has a precision of only 11–93 percent, whereas in the present method of direct detection, the CV is always less than 15 percent for peak area (total fluorescence). The precision (CV) of peak position in the gel (lapsed time) is less than 1 percent. In hybridization assays of actual patient specimens producing RNA-DNA hybrids, reliable and quantitative detection of less than 2000 equivalents of HIV could be achieved.

The technique of capillary electrophoresis (CE) is utilized in the present method. A discussion of methods applicable to the Beckman instrument used in the experiments set forth in the Examples is given in Altria, et al., *Quantitative Applications of Capillary Electrophoresis in Pharmaceutical Analysis*, Beckman:1994, Publication No. 538703, and Altria, *Capillary Electrophoresis Guidebook*, Humana Press: 1995. CE has been applied to direct quantitation of HIV-1 in patients having high serum levels of HIV-1. Ferandez-Arcas, et al., *J. Acq. Immune Defic. and Hum. Retrobiol.*, 12: 107 (1996) reported detection by direct UV analysis of extracted RNA at levels of greater than $10^8$ virions/ml correlated to the very high levels of circulating virus in early infection. This direct technique, even with the enhancement expected with laser-induced fluorescence is not sensitive enough to monitor anti-HIV drug therapy where levels of circulating virus decline. For further comprehensive materials on conventional methods and applications of capillary electrophoresis, please see Landers, *Handbook of Capillary Electrophoresis*, CRC Press: 1997.

Other advantages of the present invention will be apparent from the Examples which follow.

EXAMPLE 1
Sample Collection and RNA Extraction

RNA was obtained from a HIV seropositive patient by centrifugation of whole blood at 3,000×g for 15 min at 4° C. on a Centra GP8R (International Equipment Corporation, Needham Heights, Mass., U.S.A.) refrigerated centrifuge. The plasma was separated and stored at −80° C. RNA was extracted from plasma samples using the Ultraspec II RNA isolation system (Biotex, Houston, Tex., U.S.A.) as recommended by the manufacturer. RNA was extracted from both plasma and peripheral blood lymphocytes of a HIV seronegative normal volunteer. RNA was also obtained from *Spodoptera frugiperda* 21, grown in TC-100 serum (HyClone, Logan, Utah, U.S.A.) at 27° C. RNA was resuspended in DPEC treated water (Biotex, Houston, Tex., U.S.A.) and quantitated spectrophotometrically.

Probe Synthesis and Hybridization

To ensure specificity, a unique gene sequence is probed. The pol region is the most genetically unique of the HIV genome and a 26 bp sequence in this region was selected (GenBank entry U62632). Uniqueness was verified by a GenBank search. A 5'-fluorescein phosphoramidite (Glenn Research, Sterling, Va., U.S.A.) (probe sequence=5'-ACAGTATTAGAAGAYATGRRTTTGCC-3') labeled DNA probe for this sequence was synthesized by the University of Wisconsin Biotechnology Center (Madison, Wis., U.S.A.). Sample RNA present in a concentration of 0.095 μg/μL was diluted serially with DEPC treated water and hybridized with the DNA probe (1.0125 μg) in a buffer volume of 30 μL containing 10 mM Tris-HCl (pH 7.2), 1 mM EDTA (pH 8.0), 50 mM NaCl, and 1 mM cetyltrimethylammonium bromide (CTAB) (ACROS, Pittsburgh, Pa., U.S.A.). The mixture was heated at 85° C. for 10 min, and then incubated at 42° C. for 4 h. The addition of CTAB to the hybridization, as reported by Pontius, et al., *Proc. Natl. Acad. Sci.*, 88:8237 (1991).

Following incubation, samples were digested for 30 min at 37° C. with RNAase One (4.5 U) (Promega Corporation, Madison, Wis., U.S.A.) in a digestion buffer of 50 μL consisting of 50 mM Tris-HCl (pH 7.2), 5 mM EDTA (pH 8.0). Samples were flash frozen at −80° C. to stop enzymatic digestion.

EXAMPLE 2
CE-LIF Analysis

Separations were performed on a P/ACE 2050 CE system (Beckman Instruments, Fullerton, Calif., U.S.A.) with the temperature held constant at 20° C. Detection of hybridization samples was achieved using laser-induced fluorescence in the reversed-polarity mode (anode at the detector side) at excitation of 488 nm and emission of 520 nm. Samples were introduced hydrodynamically by 10 s injections at 0.34 Pa across a 65 cm×100 μm coated eCAP dsDNA capillary filled with replaced linear polyacrylamide (Beckman Instruments, Fullerton, Calif., U.S.A.). The capillary was conditioned with eCAP dsDNA 1000 gel buffer which contained 60 μL of LiFluor dsDNA 1000 EnhanceCE (thiazole orange) intercalator per 20 mL (Beckman Instruments, Fullerton, Calif., U.S.A.). Separation were performed under constant voltage at 7.0 kV for 15–30 min. The capillary was rinsed with gel buffer for 3 min prior to each injection. The capillary was calibrated with the fluorescently labeled probe and a mixture of RNA molecular markers (Ambion, Austin, Tex., U.S.A.). The 5 markers ranged in size from 100–500 bp. Postrun analysis of data was performed using the System Gold chromatography data system (Beckman Instruments, Fullerton, Calif., U.S.A.).

Referring to Table 1, the stabilities of various calibrator RNA standards is given. The low CV percentages indicate that CE is highly precise with respect to variation both in terms of total fluorescence (peak area) and migration time on the gel.

TABLE 1

Stability of Cellular RNA at Room Temperature

| Peak Injection | Peak Area | | | | |
|---|---|---|---|---|---|
| | 5S | 16S | 18S | 23S | 28S |
| Time 0 | 1523 | 2891 | 586 | 2717 | 921 |
| Time 30 min | 1277 | 2605 | 650 | 2368 | 1002 |
| Time 60 min | 1371 | 2603 | 598 | 2183 | 911 |
| Mean | 1390.33 | 2699.67 | 611.33 | 2422.67 | 944.67 |
| St dev | 124.13 | 165.70 | 34.02 | 271.1 | 49.9 |
| CV % | 8.9 | 6.1 | 5.5 | 11 | 5 |
| % change over 30 min | −17 | −10 | +10 | −13 | −8 |
| % change over 60 min | −10 | −10 | +2 | −20 | −1 |
| Injection | Migration Time | | | | |
| Time 0 | 11.96 | 12.17 | 13.45 | 14.58 | 16.68 |
| Time 30 min | 11.94 | 12.21 | 13.44 | 14.54 | 16.64 |
| Time 60 min | 11.94 | 12.20 | 13.45 | 14.55 | 16.66 |
| Mean | 11.95 | 12.19 | 13.45 | 14.56 | 16.66 |
| St dev | 0.012 | 0.021 | 0.006 | 0.021 | 0.02 |
| CV % | 0.1 | 0.1 | 0.04 | 0.1 | 0.1 |

Table 2 compares the detection limits and reproducibility for duplex combination of RNA/RNA, RNA/DNA, and DNA/DNA. The lower detection limit for DNA/DNA is explained by the greater known number of dye molecules intercalating that duplex than for RNA/RNA. All CV values were less then 15 percent.

TABLE 2

Comparison of Detection Limits and Reproducibility of Various Nucleotide Complexes

| | Minimum Detectable Quantity | | Precision | |
|---|---|---|---|---|
| Nucleotide Complex | Weight | HIV equivalents | Migration Time CV % | Peak Area CV % |
| RNA/RNA | 500 fg | 50,000 | 0.16–1.1 | 0.9–1.0 |
| DNA/DNA-Fluorescein | 36 ag | 4 | 0.18–0.22 | 7.3–11 |
| DNA/RNA-Fluorescein | 190 ag | 21 | 0.18–0.22 | 5.6–7.3 |

Table 3 shows that the total fluorescence when both a terminal dye and an intercalating dye are used is additive when emission takes place at the same wavelength. The low panel shows the dramatic contribution to duplex stability of the dye combination.

TABLE 3

1. Synergy Experiment: DNA/DNA hybrids

| Dye | Peak Area (rounded to nearest 10,000 rfu) |
|---|---|
| FL alone | 90,000 |
| TO alone | 10,000 |
| FL + TO | 100,000 |

2. Stability Experiment DNA/RNA hybrids

| Complex | Degradation (% decrease in peak area) | Retention time CV |
|---|---|---|
| FL + TO | <5% | <0.5% |
| FL | 41–45% | >70% |
| TO | 31–33% | 1% |

EXAMPLE 3
Analysis of Low Copy HIV RNA by Addition of Carrier RNA

Serum obtained from HIV seropositive patient #31 was serially diluted with sterile double distilled $H_2O$. The original sample contained $5 \times 10^5$ HIV copies per ml and five dilutions were made, the most dilute containing 10 copies of HIV RNA per ml. *E. Coli* tRNA (100 mcg) was added to the diluted samples, and the hybridizations to labelled probe were carried out.

RNA was then extracted by Ultraspec II RNA Isolation System, hybridized as usual and analyzed by CE-LIF.

TABLE 4

| Copies HIV per ml scrum | Weight equivalent | Peak Area (ND = not detectable) |
|---|---|---|
| $5 \times 10^5$ | 50 pcg | 9768 |
| $10^5$ | 10 pcg | 2437 |
| $10^4$ | 1 pcg | ND |
| $10^3$ | 100 fmt | ND |
| $10^2$ | 10 fmt | ND |
| 10 | 1 fmt | ND |

The failure to detect viral RNA at higher dilutions indicates that the hybrids are unstable, even in the presence of carrier tRNA. Contrast this to extracting RNA then serially diluting. Detection limits are 1.9 fg for DNA/RNA complexes.

What is claimed is:

1. A method for direct quantitation of an RNA sequence present in a sample in low copy number comprising
    extracting the RNA from a biological specimen
    hybridizing said RNA to a fluorescent DNA probe having a complementary sequence to said RNA to form a RNA-DNA hybrid
    applying said RNA-DNA hybrid to a capillary electrophoresis column
    electrophoresing said hybrid in a band under an electric current applied to said capillary column in the presence of a dye capable of intercalating double stranded nucleic acids, and
    quantitatively detecting said RNA-DNA hybrid by measuring the total fluorescent intensity of light emitted from said hybrid band upon excitation by laser-induced fluorescence.

2. A method for direct quantitation of an RNA sequence present in a sample comprising
    extracting the RNA from a biological specimen
    hybridizing said RNA to a fluorescent DNA probe having a complementary sequence to said RNA to form an RNA-DNA hybrid
    loading said RNA-DNA hybrid onto a capillary electrophoresis column having a matrix containing a dye capable of intercalating double stranded nucleic acids
    applying an electric current through the matrix of said column to effect electrophoresis of said RNA-DNA hybrid in a hybrid band, and
    quantitatively detecting said RNA-DNA hybrid by measuring the total fluorescence of light emitted from said hybrid band upon excitation by laser-induced fluorescence.

3. A method for stabilizing during capillary electrophoresis nucleic acid hybrids consisting of an RNA strand and a fluorophore terminally labelled DNA strand 15 to 40 base pairs in length comprising electrophoresing said nucleic acid hybrids in the presence of a dye capable of intercalating double stranded nucleic acids.

4. A direct quantitative test kit of for an RNA sequence suspected of being present in a biological specimen utilizing capillary electrophoresis and laser-induced fluorscence comprising A DNA probe of 15 to 30 nucleotides terminally labeled with a fluorophore a the 5' end and having a sequence complementary to a target RNA sense sequence, and a dye capable of intercalating a RNA-DNA hybrid molecule of 15–30 base pairs, wherein said RNA sequence is an RNA strand conforming to Seq. I.D. Nos. 1–12.

5. The method of claims 1 or 2 wherein said RNA sequence is a portion of the sequence encoding the HIV-1 genome.

6. The method of claim 1 or 2 wherein said RNA sequence is a 25 base sense strand segment conforming to Seq. I.D. No. 1.

7. The method of claims 1, 2 or 3 wherein said dye is selected from the group consisting of thiazole orange and YoYo.

\* \* \* \* \*

UNITED STATES PATENT AND TRADEMARK OFFICE
CERTIFICATE OF CORRECTION

PATENT NO. : 6,013,442
DATED : January 11, 2000
INVENTOR(S) : Jill M. Kolesar and Peter G. Allen Page 1 of 1

It is certified that error appears in the above-identified patent and that said Letters Patent is hereby corrected as shown below:

Title page,
Item [73], should read as follows: Assignee: Wisconsin Alumni Reasearch Foundation, Madison, Wis.

Signed and Sealed this

Fourteenth Day of August, 2001

Attest:

NICHOLAS P. GODICI
Attesting Officer
Acting Director of the United States Patent and Trademark Office

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 26 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:1:

ACAGTATTAG AAGAMATGRR TTTGCC      26

(2) INFORMATION FOR SEQ ID NO:2:

(i) SEQUENCE CHARACTERISTICS:
      (A) LENGTH: 26 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:2:

GGCAAARRCA TMTCTTCTAA TACTGT      26

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: single
      (D) TOPOLOGY: linear    (ii) MOLECULE TYPE: DNA (genomic)

(xi) SEQUENCE DESCRIPTION: SEQ ID NO:3:

TCGGACCTCT ATGCCATGAA CT                          22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

AGTTCATGGC ATAGAGGTCC GA                          22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGGCTGGTTT GAGCGAGTGT TC                          22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAACACTCGC TCAAACCAGC CT                          22

(2) INFORMATION FOR SEQ ID NO:7:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CAGCAGACGC CCGAATTCAA AT                          22

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

ATTTGAATTC GGGCGTCTGC TG                          22

-continued (2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:9:

AGAGACCTCG AGATGAGGAT GA              22

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:10:

TCATCCTCAT CTCGAGGTCT CT              22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:11:

TCTCGTATTT CTGCCAGTCC TT              22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: DNA (genomic)

(xi) SEQUENCE DESCRIPTION: SEQ ID NO:12:

AAGGACTGGC AGAAATACGA GA              22